United States Statutory Invention Registration [19]

[11] Reg. Number: H214

Little [43] Published: Feb. 3, 1987

[54] DISTILLATION PROCESS FOR THE ISOLATION OF 1,1-DIFLUORO(MONO- OR DIHALO)ETHOXYBENZENEAMINES

[76] Inventor: John C. Little, 5450 Kirkwood Dr. #C-2, Concord, Calif. 94521

[21] Appl. No.: 756,907

[22] Filed: Jul. 19, 1985

[51] Int. Cl.[4] ..... C07C 93/14; C07C 43/225; C07C 41/42

[52] U.S. Cl. ..... 564/437; 564/442; 568/655

[58] Field of Search ..... 564/437, 442; 568/655; 260/465 E

[56] References Cited

U.S. PATENT DOCUMENTS

| | | | |
|---|---|---|---|
| 3,277,068 | 10/1966 | Wall et al. | 568/655 |
| 3,926,989 | 12/1975 | Rebsdat et al. | 568/655 |
| 4,423,249 | 12/1983 | Carl et al. | 568/655 |

OTHER PUBLICATIONS

"The Merck Index" ed. Windholz, M., 10th ed. 1983, pp. 679, 1067, 7093.

Sax, N. I. *Dangerous Properties of Industrial Materials,* 6th ed., pp. 280–282, 360–362 and 2162.

*Primary Examiner*—John F. Terapane
*Assistant Examiner*—J. E. Thomas

[57] ABSTRACT

Substituted 1,1-difluoro(mono- or dihalo)ethoxybenzeneamines prepared by the reaction of a 1,1-difluoro(-mono- or dihalo)ethylene and a substituted hydroxybenzeneamine in the presence of an alkali or alkaline earth metal hydroxide and a polar, aprotic solvent are isolated from the reaction mixture by a two stage distillation without prior dilution with water or other means of removal or neutralization of the alkali or alkaline earth metal hydroxides present. The products are useful intermediates in the preparation of insecticides and herbicides.

13 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

DISTILLATION PROCESS FOR THE ISOLATION OF 1,1-DIFLUORO(MONO- OR DIHALO)ETHOXYBENZENEAMINES

BACKGROUND OF THE INVENTION

Commercially feasible and economical processes for the manufacture of substituted 1,1-difluoro(mono- or dihalo)ethoxybenzeneamines are desirable because these compounds are useful as intermediates in the preparation of valuable substances, such as agricultural herbicides and pesticides. Thus, substituted 1,1-difluoro(mono- or dihalo)ethoxybenzeneamines are employed as intermediates in the preparation of the corresponding acyl ureas which are useful as insecticides (see, for example, U.S. Pat. Nos. 3,761,486 and 4,468,405). Similarly, certain aryloxyphenoxypropionanilides, which are useful for the selective control of graminaceous weeds (see Ser. No. 730,353 filed May 2, 1985), are readily synthesized by employing these compounds as intermediates.

Substituted difluoro(mono- or dihalo)ethoxybenzeneamines are generally prepared by the reaction of 1,1-difluoro(mono- or dihalo)ethylenes with hydroxybenzeneamines in the presence of an alkali metal or alkaline earth metal hydroxide and in a polar, aprotic, water-miscible solvent as described, for example, in U.S. Pat. No. 3,926,898. The reactions proceed well and the desired products are formed in good yield. Isolation of the products from the reaction mixtures obtained, however, has proved to be difficult and the methods conventionally employed do not lend themselves to commercial operations. Thus, the isolation procedures described to date for recovering substituted 1,1-difluoro(mono- or dihalo)ethoxybenzeneamines prepared in this manner all involve dilution of the reaction mixture with water to insolubilize the product and subsequent separation of the product containing oil or solid phase that forms from the aqueous phase. Normally this is accomplished with the aid of another, water-immiscible solvent. Thus, in a typical procedure, the reaction mixture obtained is diluted with water and methylene chloride to obtain a biphasic liquid mixture. The two phases are separated and the methylene chloride phase is distilled to remove the methylene chloride, leaving the desired product in crude form as a residue. The crude substituted 1,1-difluoro(mono- or dihalo)ethoxybenzeneamine products thus obtained have been further purified by conventional means such as distillation and crystallization. Such isolation procedures have little value for commercial operations because the separation of the organic and aqueous phases present after the addition of water is very difficult, costly and time consuming, due to the formation of emulsions and the fact that both phases are very dark in color. Furthermore, the recovery and purification of the polar, aprotic, water-miscible solvent from the aqueous phase for recycle, which is important for commercial operations, is expensive and difficult. The recovery and purification of the optionally employed water-immiscible solvent for recycle further adds to the expense.

The isolation schemes defined hereinabove, which are currently employed for the isolation of substituted 1,1-difluoro(mono- or dihalo)ethoxybenzeneamines, were all designed to avoid further reactions of the products with the alkali metal or alkaline earth metal hydroxides present in the reaction media, which reduce the yields and additionally complicate the isolation of the products. The further, deleterious reactions known to take place include dehydrofluorination, hydrolysis, and conversion to orthoformate esters. These reactions are analogous to the degradative reactions of alkyl 1,1-difluoro(mono- or dihalo)ethyl ethers discussed in J. Am. Chem. Soc. 73, 1781(1951). The known isolation schemes avoid such reactions by physically separating the alkali metal or alkaline earth metal hydroxides from the desired products by virtue of the solubility of such hydroxides and insolubility of the products in aqueous media.

SUMMARY OF THE INVENTION

The present invention relates to a process for the isolation of products from the reaction mixture obtained on preparation of the compounds by treatment of hydroxybenzeneamines with a 1,1-difluoro(mono- or dihalo)ethylene in the presence of an alkali metal or alkaline earth metal hydroxide by distillation, without prior removal or neutralization of the alkali metal or alkaline earth metal hydroxides present.

It has now been found that substituted 1,1-difluoro(mono- or dihalo)ethoxybenzeneamines corresponding to the formula

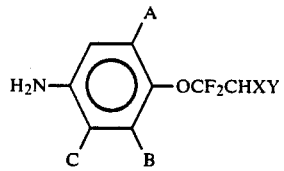

(I)

wherein

A, B, and C each independently represent —H, —F, —Cl, —Br, —CN, —$C_1$–$C_4$ alkyl or —$C_1$–$C_4$ alkoxy, X represents —F, —Cl, or —Br, and Y represents —F, —Cl, —Br, or —H, prepared by the reaction of a 1,1-difluoro(mono- or dihalo)ethylene with a hydroxybenzeneamine in the presence of an alkali metal or alkaline earth metal hydroxide and a polar, aprotic solvent, can be isolated from the reaction mixture thus obtained by a two stage distillation procedure in which in the first stage the solvent is removed and in the second stage the desired compound is obtained in relatively pure form as a distilled product. The isolation process of this invention is simple and can be readily employed in commercial operations. Dilution with water is avoided, thereby, eliminating the problems associated with phase separation and greatly simplifying the recovery and purification of the reaction solvent for recycle. The use of a second, water-immiscible solvent to aid in the phase separation, with its attendant problems of recovery and purification for recycle, has been obviated. The cost of producing 1,1-difluoro(mono- or dihalo)ethoxybenzeneamines using the present invention is greatly reduced as fewer raw materials, less energy, and fewer process steps are required. The present process now makes the recovery of the 1,1-difluoro(mono- or dihalo)ethoxybenzeneamines a commercially feasible operation.

The operability of the present invention is surprising in view of the known instability of 1,1-difluoro(mono- or dihalo(mono- or dihalo)ethoxybenzeneamines in the presence of alkali metal or alkaline earth metal hydroxides and the fact that heat, which would be expected to accelerate the degradative reactions, is applied to the reaction mixtures to effect the distillations employed. Extensive degradation would be expected, but is not experienced.

The isolation procedure of this invention can be employed to obtain substituted 1,1-difluoro(mono- or dihalo)ethoxybenzeneamines prepared by the reaction of 1,1-difluoro(mono- or dihalo)ethylenes and substituted hydroxybenzeneamines in the presence of an alkali metal or alkaline earth metal hydroxide and a polar, aprotic solvent according, for example, to the teachings of U.S. Pat. No. 3,926,898, J. Am. Chem. Soc., 82 5116 (1960), J. Org. Chem., 29 1 (1964), and J. Am Chem. Soc., 73, 1781 (1951). The specific manner in which the reaction is carried out is not important to this invention. At the conclusion of the reaction period, the mixture obtained is distilled in two stages using conventional distillation procedures and apparatus. The solvent and any other low boiling substances present are removed as distillate in the first stage. The first stage distillation can be carried out using a conventional procedure and apparatus at atmospheric or under reduced pressure depending on the boiling point of the solvent and the apparatus employed. The substituted 1,1-difluoro(mono- or dihalo)ethoxybenzeneamine product, which remains in the residue of the first stage distillation, is then recovered as a distillate in the second stage distillation employing reduced pressure and using conventional distillation procedures and apparatus.

The process of the present invention is useful in the isolation of substituted 1,1-difluoro(mono- or dihalo)ethoxybenzeneamines of Formula I wherein A, B, C, X, and Y are as defined hereinabove. Representative compounds of Formula I, which may be isolated by the method of the invention, include the following:

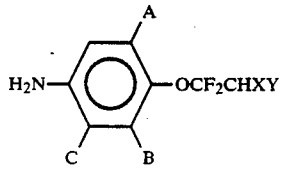

| Compound | X | Y | A | B | C |
|---|---|---|---|---|---|
| 1 | —F | —F | —Cl | —Cl | —H |
| 2 | —Cl | —F | —Cl | —Cl | —H |
| 3 | —Br | —F | —Cl | —Cl | —H |
| 4 | —Cl | —F | —$CH_3$ | —$CH_3$ | —H |
| 5 | —Cl | —F | —H | —H | —H |
| 6 | —F | —F | —H | —H | —H |
| 7 | —Br | —F | —Cl | —H | —Cl |
| 8 | —Cl | —F | —Cl | —H | —Cl |
| 9 | —F | —F | —Cl | —H | —Cl |
| 10 | —Cl | —Cl | —Cl | —Cl | —Cl |
| 11 | —Br | —Br | —Br | —H | —H |
| 12 | —F | —H | —$OCH_3$ | —H | —CN |
| 13 | —Cl | —H | —H | —H | —$C_4H_9$ |
| 14 | —F | —F | —Cl | —H | —H |
| 15 | —Cl | —Cl | —H | —H | —H |

The reaction mixtures from which the substituted 1,1-difluoro(mono- or dihalo)ethoxybenzeneamines are isolated according to the present invention contain, in addition to the product, one or more polar, aprotic solvents such as N,N-dimethylformamide, N,N-dimethylacetamide, N-methylpyrrolidone, N,N,N',N',N'',N''-hexamethylphosphoric triamide, N,N,N',N'-tetramethylurea, dimethylsulfoxide, dimethylsulfone, sulfolane, dioxane, 1,2-dimethoxyethane, acetonitrile and the like. They also contain one or more alkali metal or alkaline earth metal hydroxides such as lithium, sodium, potassium, magnesium, or calcium hydroxide. Other components in addition to those named may also be present in the reaction mixtures.

The reaction mixtures used in this invention may be filtered to remove particulates, if desired, or distilled without any further treatment. The first stage distillation, which removes solvents and other low boiling components can be carried out in any ordinary batch or continuous distillation apparatus, with or without a fractionating column and with or without a means of controlling the reflux ratio. Pressures of from 0.1 to 760 mm Hg can be employed, but it is preferable to conduct the distillation under a pressure sufficiently reduced so that the majority of the solvent will distill from the mixture at a temperature below 120° C. and more preferably below 80° C. The subsequent stage distillation which removes the desired 1,1-difluoro(mono- or dihalo)ethoxybenzeneamines from the residue of the first stage distillation as a distillate, can also be carried out in any ordinary batch or continuous distillation apparatus, with or without a fractionating column and with or without a means of controlling the reflux ratio. It is preferable to utilize a flash distillation apparatus such as a Kugelrohr still, falling film still or wiped film still. Pressures from 0.01 to 20 mm Hg can be employed, but it is preferable to conduct the distillation at a pressure sufficiently low that essentially all of the product substituted 1,1-difluoro(mono- or dihalo)ethoxybenzeneamine will distill at a temperature below 200° C. and more preferably below 150° C.

The 1,1-difluoro(mono- or dihalo)ethoxybenzeneamines isolated by the improved process of this invention are useful either as obtained or after additional purification.

The following example is provided as an illustration of the invention and should not be construed as limiting the scope of the invention in any way.

EXAMPLE 1

Preparation and isolation of 3,5-dichloro-4-(1,1,2,2-tetrafluoroethoxy)benzeneamine.

To a 2 liter, 3 necked flask equipped with an efficient stirrer, reflux condenser, fritted glass sparger, thermometer, heat lamp regulated by a controller, and a U-tube bubbler sealed to the top of the condenser was charged 356 g (2.0 moles) of 2,6-dichloro-4-aminophenol, 26 g (0.4 mole) of powdered potassium hydroxide and 1300 ml of N,N-dimethylformamide (DMF). The opaque, purple-black mixture obtained was heated to 80° C. while tetrafluoroethylene gas was added through the sparger. When the temperature reached 80° C., the tetrafluoroethylene flow rate was increased. A moderate exotherm prevailed for about 2 hours at which point the rate of tetrafluoroethylene uptake began slowing. The addition was continued for a total of 3.5 hours.

The resulting purple-black, opaque mixture was distilled without neutralization under reduced pressure in a rotary evaporator to remove most of the DMF. The final bath temperature was 80° C. at 1 mm pressure. The crude product was transferred to a Kugelrohr (bulb-to-bulb) distillation apparatus and distilled at 0.2–1.0 mm pressure and an air bath temperature up to 150° C. to obtain 545 g of a pale yellow oil which contained by g.c. analysis 15 percent DMF and 83.4 percent 3,5-dichloro- 4-(1,1,2,2-tetrafluoroethoxy)benzeneamine, for a net yield of 82 percent.

A purified sample of the product was obtained by subsequent fractional distillation using an approximately 10 theoretical plate Vigreux column, b.p. 126° C./4 mm. The proton and fluorine nuclear magnetic resonance (NMR) spectra confirmed this to be the title compound.

I claim:

1. A process for the isolation of 1,1-difluoro-(mono- or dihalo)ethoxybenzeneamines

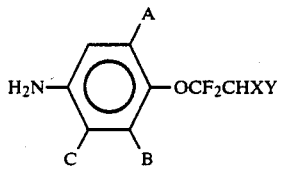

wherein

A, B, and C each independently represent —H, —F, —Cl, —Br, —CN, —$C_1$–$C_4$ alkyl, or —$C_1$–$C_4$ alkoxy, X represents —F, —Cl or —Br, and Y represents —F, —Cl, —Br or —H, prepared by the reaction of a 1,1-difluoro(mono- or dihalo)ethylene with a hydroxybenzeneamine in the presence of an alkali metal or alkaline earth metal hydroxide and a polar, aprotic solvent, which comprises distilling the reaction product in two stages so that the solvent and other volatile constituents are removed from the reaction mixture in the first stage by distillation at or below atmospheric pressure and the product is isolated from the residue of the first stage in the second stage by distillation under reduced pressure, without prior dilution with water and phase separation or prior treatment to neutralize said alkali metal or alkaline earth metal hydroxide.

2. A process according to claim 1 wherein X and Y represent F.

3. A process according to claim 2 wherein the product obtained is 3,5-dichloro-4-(1,1,2,2-tetrafluoroethoxy)benzeneamine.

4. A process according to claim 2 wherein the product obtained is 4-(1,1,2,2-tetrafluoroethoxy)benzeneamine.

5. A process according to claim 1 wherein X represents F and Y represents Cl.

6. A process according to claim 5 wherein the product obtained is 3,5-dichloro-4-(2-chloro-1,1,2-trifluoroethoxy)benzeneamine.

7. A process according to claim 5 wherein the product obtained is 3,5-dimethyl-4-(2-chloro-1,1,2-trifluoroethoxy)benzeneamine.

8. A process according to claim 5 wherein the product obtained is 4-(2-chloro-1,1,2-trifluoroethoxy)benzeneamine.

9. A process according to claim 1 wherein the product obtained is 4-(1,1-difluoro-2,2-dichloro)benzeneamine.

10. A process according to claim 1 wherein the pressure of the solvent removal distillation is sufficiently reduced that the temperature in the distillation apparatus does not exceed 120° C.

11. A process according to claim 1 wherein the pressure of the product isolation distillation is sufficiently reduced that the temperature in the distillation apparatus does not exceed 200° C.

12. A process according to claim 1 wherein the polar, aprotic solvent is N,N-dimethylformamide.

13. A process according to claim 1 wherein the alkali metal or alkaline earth hydroxide is potassium hydroxide.

* * * * *